United States Patent [19]
Roberts, II et al.

[11] Patent Number: 5,858,696
[45] Date of Patent: *Jan. 12, 1999

[54] METHOD AND COMPOSITIONS TO ASSESS OXIDATIVE STRESS IN VIVO

[75] Inventors: L. Jackson Roberts, II; Jason D. Morrow, both of Nashville, Tenn.

[73] Assignee: Vanderbilt University, Nashville, Tenn.

[*] Notice: The term of this patent shall not extend beyond the expiration date of Pat. No. 5,700,654.

[21] Appl. No.: 912,440

[22] Filed: Aug. 18, 1997

Related U.S. Application Data

[63] Continuation-in-part of Ser. No. 304,147, Sep. 12, 1994, Pat. No. 5,700,654, which is a continuation-in-part of Ser. No. 715,419, Jun. 14, 1991, abandoned.

[51] Int. Cl.$^6$ ............................ C12Q 1/26; G01N 33/00; C07C 61/06

[52] U.S. Cl. ................................. 435/25; 435/63; 436/71; 436/74; 562/503

[58] Field of Search ................................. 435/25, 63, 71; 436/74; 562/503

[56] References Cited

U.S. PATENT DOCUMENTS 5,700,654  12/1997  Roberts et al. ............................ 435/25

*Primary Examiner*—Cecilia J. Tsang
*Assistant Examiner*—Abdel A. Mohamed
*Attorney, Agent, or Firm*—Kohn & Associates

[57] ABSTRACT

This invention relates to a method to assess oxidative stress in vivo by quantification of prostaglandin $F_2$-like compounds and their metabolites produced by a noncyclooxygenase free radical catalyzed mechanism.

10 Claims, 5 Drawing Sheets

METHOD AND COMPOSITIONS TO ASSESS OXIDATIVE STRESS IN VIVO

This application is a continuation-in-part application based on U.S. Pat. No. 08/304,147 filed Sep. 12, 1994, now U.S. Pat. No. 5,700,654, which is a continuation-in-part of Ser. No. 07/715,419 filed Jun. 14, 1991, now abandoned.

GRANT REFERENCE

The research carried out in connection with this invention was supported in part by a grant from the National Institutes of Health (NIH). This invention was made with Government support under Grant Nos. GM42056, GM15431, and DK48831. The Government has certain rights in the invention.

BACKGROUND OF THE INVENTION

1. Technical Field

This invention relates to a method to assess oxidative stress in vivo by quantification of prostaglandin-like compounds and their metabolites produced by a noncyclooxygenase free radical catalyzed mechanism.

2. Prior Art

Free radicals derived primarily from oxygen have been implicated in the pathophysiology of a number of human diseases, such as atherosclerosis, ischemia-reperfusion injury, inflammatory diseases, cancer and aging. A variety of methods have been developed to assess oxidative stress; however, some of these methods have limited sensitivity or specificity, while others are either too invasive or not adaptable for human investigation [Halliwell et al., 1987].

Free radicals are generally short lived and thus, indirect methods of detection are required [Pryor, 1989]. Standard detection methods include: electron spin resonance (directly), electron spin resonance (spin trapping), thiobarbituric acid reactive substances (TBARS), detection of malonaldehyde by direct methods (such as HPLC of malonaldehyde itself or as its dinitrophenylhydrazone derivative), detection of other oxidation products from polyunsaturated fatty acids (such as 4-hydroxynonenal), measurement of lipid hydroperoxides, detection of volatile hydrocarbons (ethane, pentane and ethylene), detection of oxidation products from lipids other than polyunsaturated fatty acids (e.g., cholesterol), oxidation of methional, methionine, or 2-keto-4-thiomethylbutanoic acid to ethylene, oxidation of benzoic acid to carbon dioxide (often with radiolabeled carbon dioxide), oxidation of phenol, benzoic acid, or aspirin to hydroxylated products, determination of decreases in antioxidant levels (e.g., decreased GSH, tocopherol, or ascorbate) or of increases in the oxidized products from antioxidants (e.g., tocopherol quinone or the ascorbyl radical), detection of oxidized DNA bases (e.g., thymine glycol, 8-hydroxydeoxyguanosine), detection of oxidized products from proteins (e.g., methionine sulfoxide from methionine) or of proteins oxidized to carbonyl-containing products that then react with hydride-reducing agents, detection of adducts of DNA bases (e.g., by enzymatic hydrolysis post-labeling using P32), and chemiluminescence methods. Id.

Unfortunately, oxidative stress is difficult to assess in humans due to lack of reliable methods to assess oxidant stress in vivo. As one author stated, "one of the greatest needs in the field now is the availability of a non-invasive test to probe the oxidative stress status of humans."Id.

Morrow et al. (1990b) discovered that a series of ($F_2$-IPs) prostaglandin $F_2$-like compounds, now termed $F_2$-isoprostanes, were generated in human plasma during storage at $-20°$ C. for several months or in plasma that had been repeatedly frozen and thawed. Morrow et al. (1990b) determined that these compounds were formed by a non-cyclooxygenase mechanism by autoxidation of arachidonic acid contained in plasma. This article demonstrated that prostaglandin-like compounds could be generated by autoxidation during storage of biological samples which could result in artifactual results with measurements of prostaglandins in stored samples. At that time, there was nothing to suggest this was anything more than just a non-enzymatic in vitro artifact or phenomenon that occurred during the storage of plasma or other lipid containing biological fluids. In fact, this process, autoxidation of lipids or fats, is a major process responsible for spoilage of food during storage.

Formation of $F_2$-isoprostanes occurs independently of the cyclooxygenase enzyme and proceeds through intermediates comprising peroxyl radical isomers of arachidonic acid, which undergo endocyclization to form bicyclic endoperoxides. The endoperoxides are then reduced to $F_2$-IPs. The endoperoxides also undergo rearrangement in vivo to form D- and E-ring IPs [Morrow, 1994a]. Four positional isomers of IPs are formed, each of which can comprise eight racemic diastereomers. IPs are initially formed esterified to phospholipids and subsequently released pre-formed [Morrow, 1992a]. Based on the mechanism of formation of IPs, i.e., the formation of compounds with the side chains oriented cis in relation to the cyclopentane ring are highly favored [Morrow et al. 1990b], one compound that would be expected to be formed would be 8-iso-$PGF_{2\alpha}$. Applicants demonstrated that 8-iso-$PGF_{2\alpha}$ is, in fact, one of the more abundant $F_2$-IPs produced in vivo [Morrow et al., 1994b]. There has been considerable interest in this molecule because it exerts biological activity, e.g., it is a potent vasoconstrictor in the lung and kidney [Takashashi, et al. 1992; Banerjee et al., 1992]. Furthermore, it has been suggested that the biological effects of 8-iso-$PGF_{2\alpha}$ may result from an interaction with a unique receptor [Fukunaga et al., 1993].

It has been recognized that one of the greatest impediments in the field of free radical research has been the lack of reliable methods to assess oxidant stress status in humans [Gutteridge et al., 1990]. A considerable body of evidence has accumulated indicating that measurement of $F_2$-IPs provide a valuable and reliable approach to assess oxidant stress in vivo both in animal models of oxidant injury and in humans [Morrow et al., 1992b; Morrow et al.; 1995]. In this regard, however, quantification of unmetabolized IPs has certain limitations. First, $F_2$-IPs can be artifactually generated ex vivo, e.g. in plasma, by auto-oxidation of plasma arachidonic acid if appropriate precautions are not taken [Morrow et al., 1990b]. In addition, quantification of $F_2$-IPs esterified in tissues or circulating in plasma only provides information at a single point in time rather than an integrated index of IP production. Having a means to obtain an integrated index of oxidant stress status would be very valuable in situations in which the level of oxidant stress fluctuates over time. In this regard, analogous to quantification of urinary metabolites of cyclooxygenase-derived prostanoids [Roberts, 1987], the measurement of the urinary excretion of $F_2$-IPs provide a reliable and integrated index of oxidative stress status in vivo.

Applicants have previously identified urinary metabolites of $F_2$-IPs that copurify through a mass spectrometric assay developed for quantification of the major urinary metabolite of cyclooxygenase-derived $PGD_2$ [Awad et al., 1993; Morrow, 1991]. However, applicants did not know the parent compounds from which these $F_2$-IP metabolites derive. Furthermore, applicants have found that a metabolite of cyclooxygenase-derived $PGF_{2\alpha}$, 9α, 11α-dihydroxy-15-oxo-13,14-dihydro-2,3,18,19-tetranorprost-1,20-dioic acid, co-chromatographs on capillary gas chromatograph (GC) with these $F_2$-IP metabolites. This latter finding confounds an interpretation as to whether an increase in the intensity of these peaks when analyzed by GC and mass spectrometry (MS) represents overproduction of $F_2$-IPs or $PGF_{2\alpha}$. Thus, 8-iso-$PGF_{2\alpha}$, was studied in order to identify its major metabolites found in human urine as a basis for the development of methods of assay for its quantification to assess oxidative stress in humans.

SUMMARY OF THE INVENTION AND ADVANTAGES

In accordance with the present invention, this invention is based on the discovery that prostanoids, particularly prostaglandin $F_2$-like compounds, are produced in vivo by a noncyclooxygenase free radical catalyzed mechanism. More specifically, it has been found that the quantity of free prostaglandin $F_2$-like compounds in plasma and urine increases in response to agents that cause free radical induced lipid peroxidation.

These prostaglandin $F_2$-like compounds are isomeric to prostaglandins produced by the cyclooxygenase enzyme and are now referred to as $F_2$ isoprostanes. The prostaglandin $F_2$-like compounds produced in response to said free radical induced lipid peroxidation have the following basic structures. Each of the four structures shown are comprised of eight racemic diastereomers:

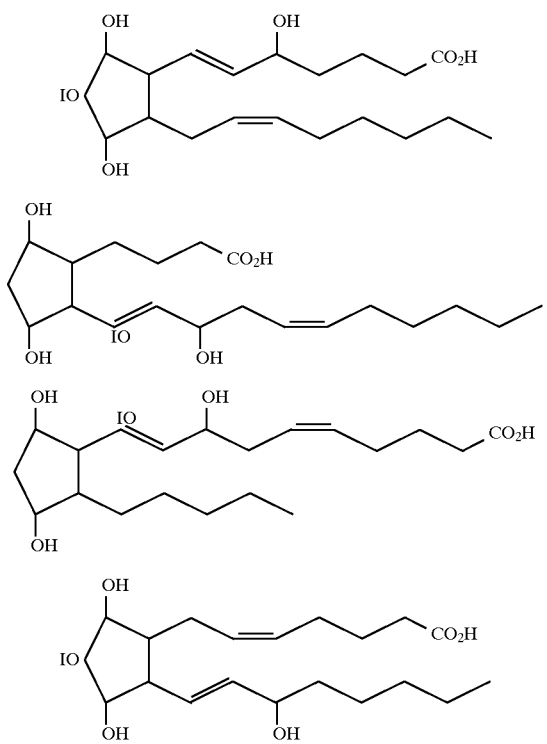

Another embodiment of this invention involves the discovery that the levels of metabolites of prostaglandin $F_2$-like compounds also increase in response to oxidative stress. The metabolites of prostaglandin $F_2$-like compounds produced in response to said free radical catalyzed mechanism have the following formula:

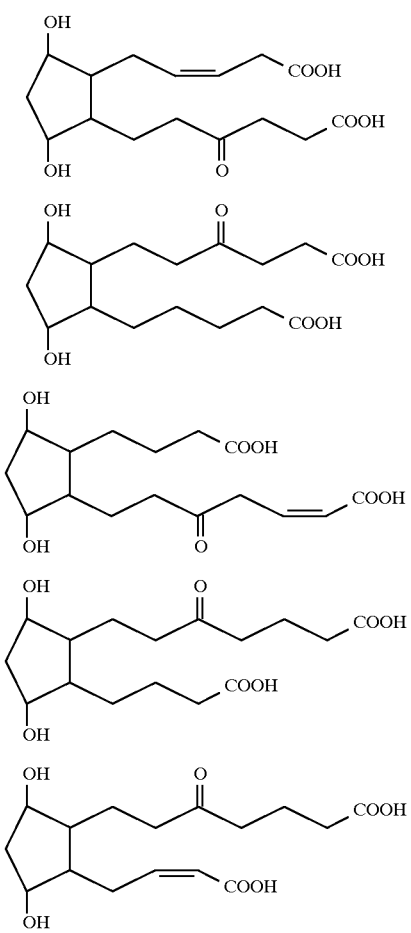

Still another embodiment involves the discovery that human tissue samples could be analyzed for prostaglandin $F_2$-like compounds.

Based on these discoveries, this invention can be used to provide a reliable method to assess oxidative stress in vivo in humans by quantifying prostaglandin $F_2$-like compounds and their metabolites. In particular, this invention provides a method to assess oxidative stress in vivo by obtaining a fresh sample of biological fluid or tissue, measuring the amount of noncyclooxygenase derived prostanoid compounds in the sample, comparing the measured amounts of the prostanoids with a control and assessing the oxidative stress in vivo based upon said comparison. It is an object of this invention to quantify these prostanoid compounds in various biological fluids including: plasma, urine, cerebrospinal fluid, bile, lung lavage fluid, lymph, and inflammatory human joint fluid. If the sample contains lipids, the measurement of noncyclooxygenase derived prostanoid compounds should be made prior to the ex vivo formation of prostaglandin $F_2$-like compounds.

Additionally, this invention provides a method to assess oxidative stress in vivo by measuring the amount of noncyclooxygenase derived metabolites of prostanoids in a fresh sample, comparing the measured amount of the metabolites of prostanoids with a control and assessing the oxidative stress in vivo.

This invention also provides a substantially pure composition of the formulas of FIG. 2 and of 2,3-dinor-5,6-dihydro-8-iso-prostaglandin $F_{2\alpha}$,

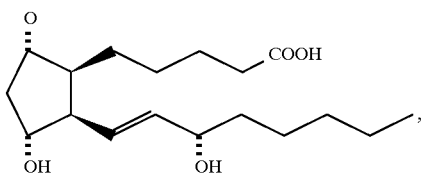

found to be the major urinary metabolite of 8-isoprostaglandin $F_{2\alpha}$. This invention may be used to assess oxidative stress in humans and it is also useful as a test for the utility of drugs such as LAZAROIDS (Upjohn Company).

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Prostaglandin $F_2$-like compounds are produced in vivo by a noncyclooxygenase free radical catalyzed mechanism. Free prostaglandin $F_2$-like compounds have been quantitated in plasma and urine. The level of individual prostaglandin $F_2$-like compounds in plasma ranges from approximately 5–50 picograms/mL and in urine from approximately 500–3000 picograms/mL.

Figure 1:
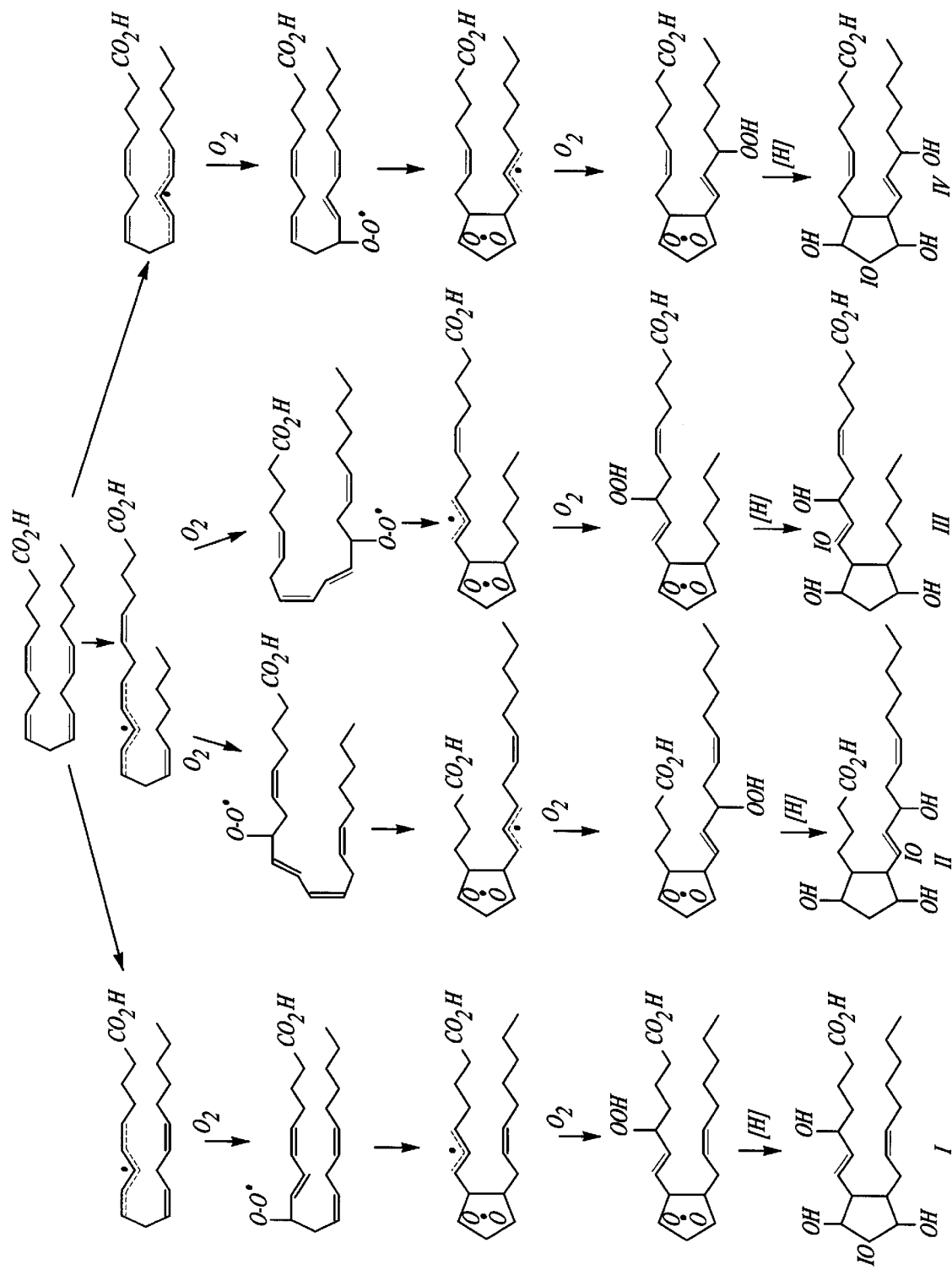
FIG. 1 shows noncyclooxygenase free radical catalyzed mechanism for the formation of prostaglandin $F_2$-like compounds and the chemical structure of four regioisomers.
Figure 2:
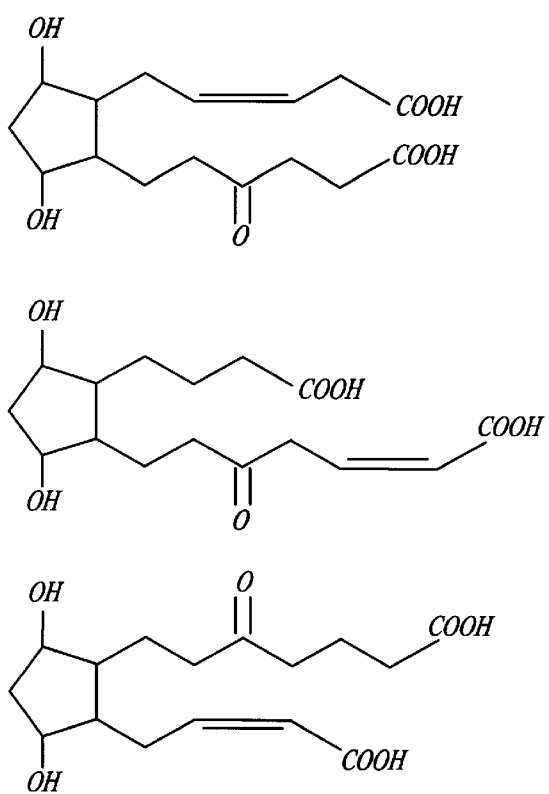
FIG. 2 shows the chemical structure of noncyclooxygenase derived prostaglandin $F_2$-like urinary metabolites.
Figure 2:
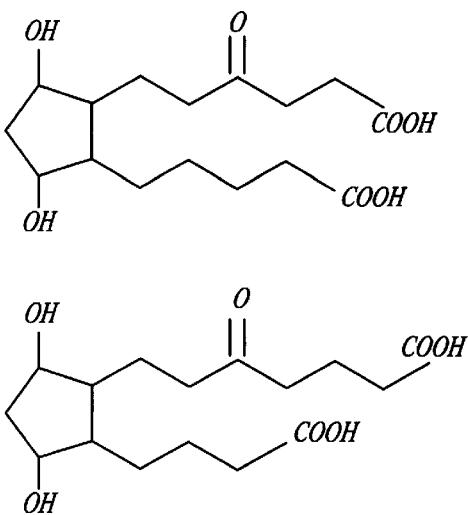
Figure 3A:
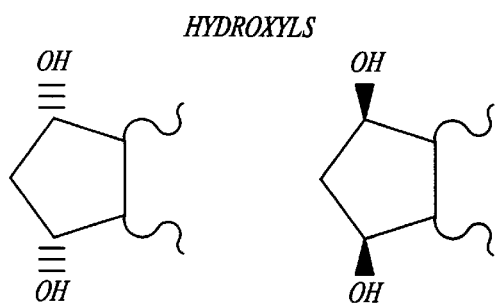
FIGS. 3A and 3B show possibilities of stereochemical changes of hydroxyls and side chains of the metabolites shown in FIG. 2.
Figure 3B:
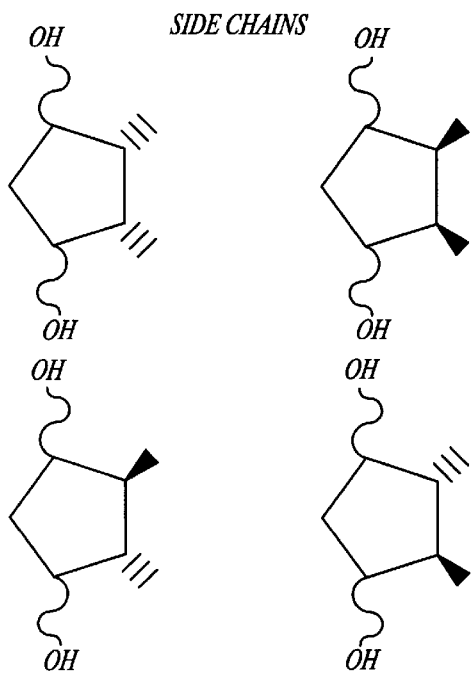

The prostaglandin $F_2$-like compounds are produced in vivo by a free radical catalyzed mechanism. In particular, electron ionization mass spectra analysis of human urine shows four prostaglandin $F_2$-like regioisomers (FIG. 1).

The quantity of free prostaglandin $F_2$-like compounds in plasma or urine increases in response to agents that cause free radical induced lipid peroxidation. Circulating levels of the compounds were shown to increase by as much as 200-fold in animal models of free radical induced lipid peroxidation. The herbicide diquat undergoes redox cycling in vivo leading to the production of superoxide anions. When diquat is administered to Se-deficient rats, marked lipid perodixation ensues. Circulating levels of prostaglandin $F_2$-like compounds in plasma obtained 1.5 hours following administration of diquat to eight Se-deficient rats were dramatically elevated from 27 to 200-fold above levels measured in Se-deficient control rats that did not receive diquat. The pattern of the elevated prostaglandin $F_2$-like compounds in treated rats also was essentially identical to the pattern seen in untreated rats.

The second animal model employed administration of carbon tetrachloride to normal rats. This leads to the formation of $CCl_3$.radicals which catalyze lipid peroxidation. Treatment of six rat carbon tetrachloride also resulted in marked increases in the circulating levels of prostaglandin $F_2$-like compounds ranging from 10 to 30-fold above normal. In addition, pretreatment of the rats with high doses of indomethacin to inhibit cyclooxygenase activity failed to suppress the production of these compounds following administration of carbon tetrachloride.

Collectively, the above results have established that there are a unique class of prostanoids that are produced in vivo by a noncyclooxygenase mechanism involving free radical catalyzed lipid peroxidation.

It should be understood that it is possible that prostaglandin $D_2$-like and prostaglandin $E_2$-like compounds may form from isomerization of prostaglandin $G_2$-like endoperoxide intermediates in aqueous solutions. Incubation of human plasma ex vivo yields significant amounts of prostaglandin $D_2$-like and prostaglandin $E_2$-like compounds when analyzed by gas chromatography selected ion monitoring negative ion chemical ionization mass spectrometry. Applicants have obtained evidence that noncyclooxygenase derived prostaglandin $D_2$-like and $E_2$-like compounds are present acylated to liver phospholipids in vivo.

Since the quantity of free prostaglandin $F_2$-like compounds in human plasma or urine increases in response to agents that cause free radical induced lipid perioxidation, an assay to measure oxidative stress in vivo was devised. Prostaglandin $F_2$-like compounds may facilitate this analysis because they are easily detected in normal human biological fluids.

Prostaglandin $F_2$-like compounds may also participate as mediators in the pathophysiology of oxidative stress. Thus, substantially purified prostaglandin $F_2$-like compounds or an antagonist of these compounds may be useful in the treatment of oxidative stress related diseases.

One drawback discovered relating to the use of these free prostaglandin $F_2$-like compounds as a means to assess oxidative stress is the ex vivo generation of prostaglandin $F_2$-like compounds in certain biological fluids. Arachidonyl containing lipids in plasma readily undergo peroxidation in vitro leading to the formation of these prostanoids. Applicants have found that plasma can be allowed to stand at room temperature for up to two hours without levels of these compounds increasing significantly. However, these compounds can be generated in substantial quantities if plasma is allowed to stand for longer periods of time, if plasma is frozen and thawed several times, or if plasma is subjected to storage at −20° C. for periods of time such as a few weeks.

The problem of artifactual generation of these compounds can be minimized, but not totally eliminated, by addition of antioxidants to the sample. Thus, to avoid these potential sources of error, plasma that is obtained for analysis should not be stored and should be processed for analysis within approximately two hours. However, it is not necessary to process the plasma sample completely through the assay. Plasma phospholipids containing arachidonic acid are the lipid source for which these compounds are generated ex vivo. Although phospholipids are generally retained by C-18 reverse phase chromatography packing, applicants have found that phospholipids in plasma are not, presumably due to binding to plasma proteins. Thus, when plasma is initially subjected to solid phase extraction using a C-18 cartridge, free prostaglandin $F_2$-like compounds present in the plasma are retained and the phospholipids are quantitatively removed in the initial aqueous phase eluate. After the retained prostaglandin $F_2$-like compounds are eluted with a 1:1 mixture of ethyl acetate:heptane, they can be stored at $-20°$ C. and processed later without the problem of ex vivo generation. Applicants have also found that whereas these prostaglandins are generated ex vivo in plasma during storage at $-20°$ C., formation of these compounds did not occur while the plasma was stored for five months at $-70°$ C.

The above discussed problem surrounding plasma undoubtedly applies to any biological fluid which contains significant quantities of lipids which can be the source of ex vivo generation of these prostanoids. However, this problem is not encountered with analysis of urine. Urine contains very few lipids and applicants have found that the levels of prostaglandin $F_2$-like compounds do not increase during storage of urine for up to six months at $-20°$ C. or during incubation of urine for seven days at $37°$ C. However, there is a potential problem associated with the quantification of these compounds in urine as an index of their systematic production. At present, applicants do not know the primary source from which the compounds present in urine are derived. Specifically, it is not known if they originate primarily from plasma via filtration by the kidney or if they arise primarily from local production in the kidney. Urinary cyclooxygenase derived prostaglandins have been shown to arise almost exclusively from local formation in the kidney. If this is also the case with the noncyclooxygenase derived prostanoids, then quantification of these compounds in urine could be used to assess oxidant stress in the kidney but this approach could not be used as an index of their systemic production.

Applicants have obtained data which provides a new dimension on the ability to assess endogenous production of these compounds which circumvents the above-discussed problems. In the process of developing a mass spectrometric assay for the major urinary metabolite of cyclooxygenase derived prostaglandin $D_2$, applicants have identified urinary metabolites of these noncyclooxygenase derived prostaglandin $F_2$-like compounds in human urine. The metabolites have the same basic atomic composition as the prostaglandin $D_2$ metabolite ($9\alpha$, 11 $\beta$-dihydroxy-15-oxo-2,3,18,19-tetranorprostane-1,20-dioic acid), but are structurally different. See FIGS. 3A, 3B, 4 and 7. The levels of metabolites of the noncyclooxygenase derived $F_2$-like compounds are not suppressed by treatment with cyclooxygenase inhibitors. Additionally, it has been found that metabolite levels increase significantly in urine following administration of carbon tetrachloride to rats. The ability to quantify a metabolite of these compounds would be extremely valuable in that it would provide an index of systemic production of these compounds without the inherent potential problem of artifactual generation of the compound ex vivo.

Still another alternative embodiment involves a discovery that tissue samples could also be analyzed for prostaglandin $F_2$, $D_2$ and $E_2$-like compounds. This observation was unexpected and surprising. Arachidonic acid is the precursor of both enzymatically derived prostaglandins and the prostaglandin $F_2$-like compounds formed by non-enzymatic peroxidation of arachidonic acid. Arachidonic acid is almost entirely stored esterified to tissue phospholipids, with only small amounts being present in free form in cells.

In enzymatic formation of prostaglandins, arachidonic acid has to be released from phospholipids by phospholipases to be metabolized by the cyclooxygenase enzyme to form prostaglandins. Once the enzymatically formed prostaglandins are produced, they are released from cells and not stored and are not found esterified to phospholipids in tissues. Thus, tissue levels of prostaglandins are essentially unmeasurable.

When phospholipids are subjected to oxidation, it is known that fatty acid hydroperoxides are formed on the phospholipids. These hydroperoxides have been shown to be readily cleaved from phospholipids by phospholipases. One question applicants investigated was whether, in contrast to cyclooxygenase derived prostaglandins, the prostaglandin $F_2$-like compounds are formed intact on phospholipids during free radical catalyzed peroxidation of lipids or whether only the oxidized precursors, i.e., the fatty acid hydroperoxides, are formed on phospholipids which are then cleaved by phospholipases and subsequently undergo the further transformation to yield prostaglandin $F_2$-like compounds. Experiments were carried out which provided direct evidence that the prostaglandin $F_2$, $D_2$, and $E_2$-like compounds are actually formed in situ esterified to phospholipids and that the levels of the compounds esterified to phospholipids in tissues of the rat following administration of $CCl_4$ to induce lipid peroxidation increased dramatically compared to levels in tissues of untreated rats.

These findings suggest another approach to assess oxidant status in tissues in some human disorders. The sensitivity of the method of detection allows applicants to detect prostaglandin $F_2$-like containing phospholipids in very small pieces of tissue well within the amount of tissue that would ordinarily be obtained in a routine biopsy. Biopsies of a variety of tissues are routinely obtained for the diagnosis of numerous types of human diseases.

For example, a number of liver diseases including alcohol liver damage are speculated to involve free radical induced injury. One problem that applicants have recognized with measuring levels of free compounds in plasma or urine or their metabolites is that local formation of these compounds at a limited site in the body may not be associated with the release of free compounds in quantities sufficient to significantly elevate the basal levels that applicants see in plasma or urine in normal humans. In these situations, it may require sampling of blood draining directly from the site of suspected pathophysiology. This can be very impractical and/or impossible in many situations in humans. However, if a biopsy is obtained of an involved tissue or organ, this approach may allow us to directly assess oxidant status in the biopsy tissue by measuring the level of prostaglandin $F_2$-like compounds esterified to tissue phospholipids. This approach could therefore be used to directly obtain evidence for the occurrence of free radical induced injury in the pathophysiology of a wide variety of human diseases.

One possible method to detect the quantity of prostaglandin $F_2$-like compounds in biological fluids is mass spectroscopy. This type of assay for prostaglandin $F_2$-like compounds or their metabolites offers several advantages. First, the mass spectrometric assay is very sensitive with a lower limit of detection in the range of one picogram. Second, the assay has a high degree of specificity and accuracy.

The present method is a stable isotope dilution assay employing capillary gas chromatography negative ion chemical ionization mass spectrometry. Heptadeuterated 9α, 11 β-prostaglandin $F_2$ or deuterated prostaglandin $F_2α$ is used as the internal standard. Prostaglandin $F_2$-like compounds are extracted by solid phase techniques using a C-18 cartridge and subsequently purified by thin layer chromatography. Analysis by mass spectrometry is accomplished as a pentaflurobenzyl ester, trimethylsilyl ether derivative. Quantification is performed by selected ion monitoring of the ratio of the M-181 (loss of ° $CH_2C_6F_6$) ions at m/z 569 for endogenous prostaglandin $F_2$-like compounds and m/z 576 for the internal standard. The assay has a precision of ±6% and an accuracy of 96%. Lower limits of detection are in the range of approximately one picogram. See FIG. 4.

The basic assay can be employed and adapted for measurement of these compounds in a wide variety of biological fluids. In addition to plasma and urine, the assay can be used with cerebrospinal fluid, bile, lung lavage fluid, lymph, and inflammatory human joint fluid.

In the alternative embodiment, the prostaglandin-like compounds can be assayed using immunoassays. Immunoassay is a suitable method for the detection of small amounts of specific prostanoids (5–500 picograms can be readily detected). In particular, antibodies can be raised to these prostaglandin-like compounds using conventional techniques. The antibodies can then be used in immunoassays to quantitate the amount of prostaglandin-like compounds in the biological fluid.

A small molecule (less than 5–10 kilodaltons) will usually not elicit the production of antibodies in experimental animals unless covalently linked to large immunogenic molecules prior to immunization. The noncyclooxygenase derived prostaglandin-like compound, such as, 8-epi-prostaglandin $F_2α$ can be coupled via its carboxyl group to a carrier protein by the dicyclohexyl-carbodiimide method [Rich et al., 1979; U.S. Pat. No. 4,859,613]. 8-epi-prostaglandin $F_2α$ can be coupled to keyhole limpet hemocyanin (KLH) by the DCC method used by Levine et al. [1980]. Accordingly, 8 mg. of 8-epi-prostaglandin $F_2α$ are dissolved in 100μl of N,N-dimethyl formamide. The 8-epi-prostaglandin $F_2α$ is then activated by the addition of 3 mg of DCC in the presence of 3.5 mg. of N-hydroxysuccinimide as a trapping agent. This reaction mixture is stirred for 30 minutes at room temperature. As the reaction proceeds, the byproduct dicyclourea will form a white precipitate. When the reaction is complete, this precipitate is removed by centrifugation. The supernatant is then added to 6.25 gm of KLH in 0.5 ml of 0.1N $NaHCO_3$ and stirred for two hours at 4° C. The conjugate is then extensively dialyzed against PBS, pH75. (0.15M NaCl, 0.005M $NaHPO_4$). The conjugate is aliquoted and stored at −20° C.

It should be noted that many unsaturated fatty acids and their derivatives, are sensitive to oxidation. However, this does not hold for prostanoids which have only a single double bond on each side chain. Prostaglandin $F_2$-like compounds are extremely stable, can withstand strong base and strong acid and are not susceptible to oxidation. Hence, although there is no facile method by which to determine the integrity of the 8-epi-prostaglandin $F_2α$ haptens attached to KLH, it is unlikely to undergo degradation or modification that could impede the production of specific antisera.

These immunogens can then be used to raise antibodies. Rabbits can be immunized with the 8-epi-prostaglandin $F_2α$-KLH conjugate administered in Complete Freund's Adjuvant. One immunization dosing and scheduling is as follows: 100 μL of conjugate in Complete Freund's Adjuvant will be administered at multiple subcutaneous sites for the primary immunization. At subsequent two week intervals 100μL of conjugate in Complete Freund's Adjuvant will be administered at multiple subcutaneous sites to boost titers. Serum will be collected from animals one week following the initial boost and titers will be determined by ELISA. Similarly, myeloma that secrete monoclonal antibodies can be prepared following the techniques described by Kohler & Milstein [1975].

These antibodies can be used in immunoassays for non-cyclooxygenase derived prostaglandin-like compounds. Typical assays for these types of compounds include enzyme-linked immunoassays, fluorescent immunoassays, and radioimmunoassays. The assays can be in the sandwich or competitive formats. See, e.g., U.S. Pat. Nos. 4,376,110 and 4,486,530.

EXAMPLE 1

Figure 4A:
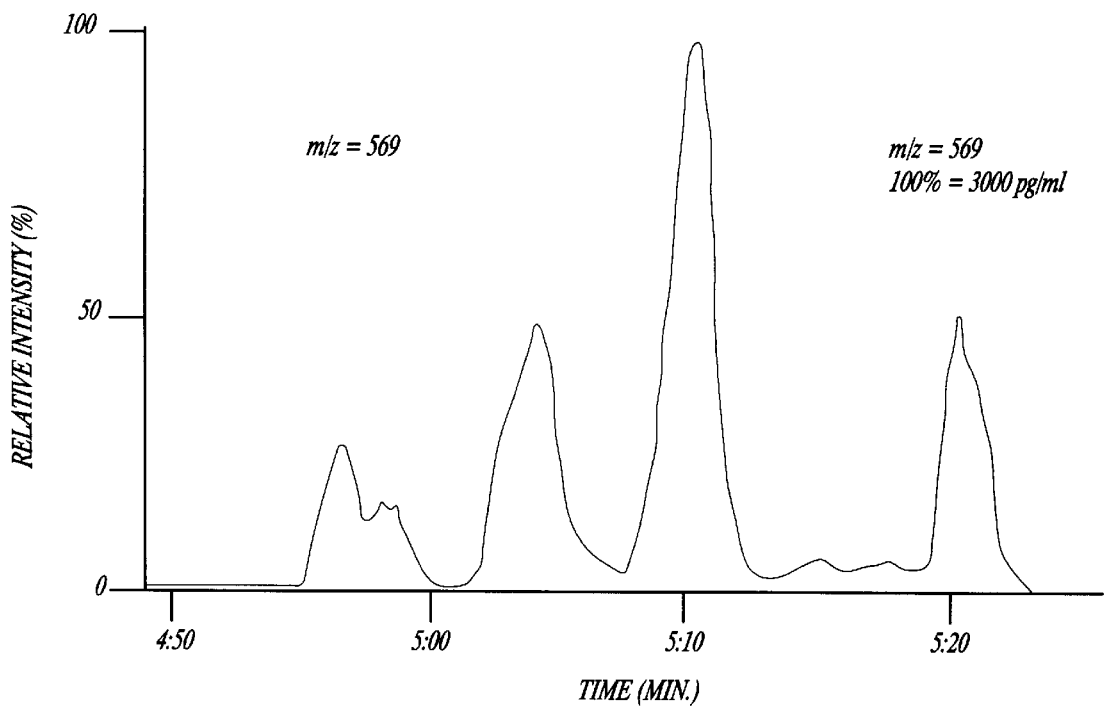
FIG. 4 shows a selected ion current chromatogram obtained from the analysis of prostaglandin $F_2$-like compounds in normal human urine. Below is the m/z 576 peak representing the $(^2H_7)9\alpha$, 11$\beta$-prostaglandin $F_2$ internal standard. At the top is the m/z 569 chromatogram which reveals a series of peaks representing endogenous urinary prostaglandin $F_2$-like compounds. Levels of the individual compounds range from approximately 500 to 3000 picogram/mL.
Figure 4B:
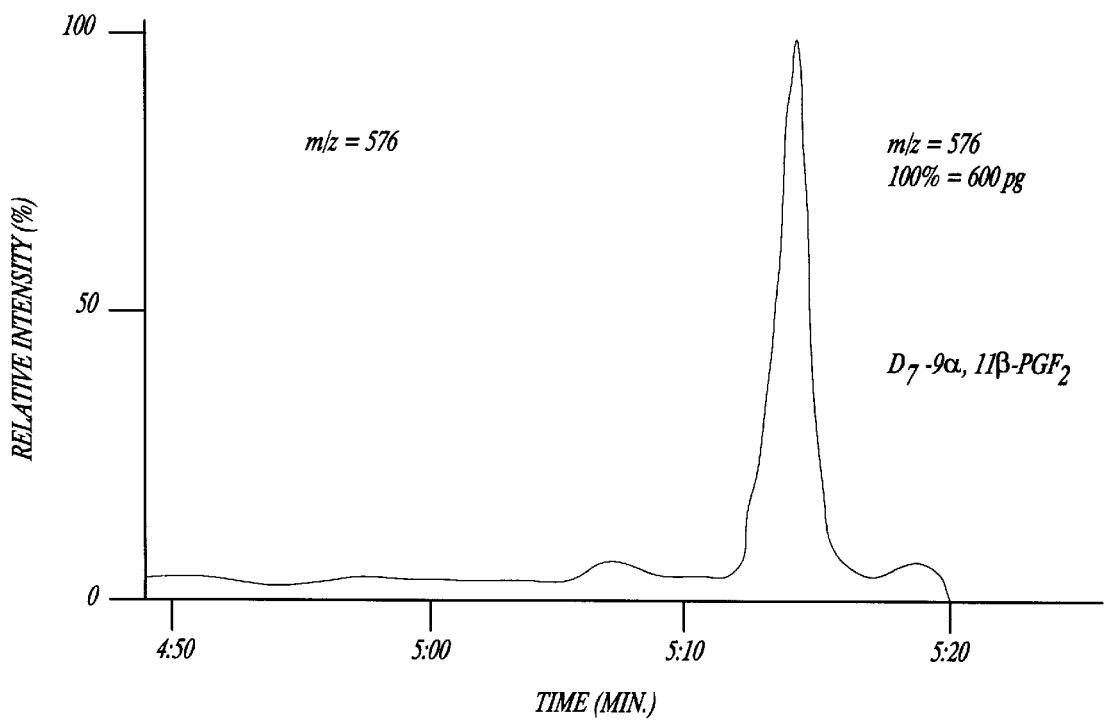

Mass spectroscopic assay for prostaglandin $F_2$-like compounds in urine. (FIG. 4).

1 mL of fresh human urine was analyzed in a stable isotope dilution assay for endogenous prostaglandin $F_2$-like compounds. At the bottom of each chromatogram is the m/z 576 peak representing the internal standard. At the top of each tracing are the m/z 569 chromatograms which reveal a series of peaks presumably representing endogenous prostaglandin $F_2$-like compounds. (See FIG. 4) The levels of the individual compounds in plasma range from approximately 5–50 picogram/ml and in urine from approximately 500–3000 picogram/ml. Employing a variety of approaches, including electron ionization mass spectral analysis of these compounds form 1 liter of human urine, it was firmly established that these peaks indeed represented regioisomers of prostaglandin $F_2$-like compounds shown in FIG. 1.

Administration of high doses of cyclooxygenase inhibitors to normal volunteers failed to suppress the levels of these compounds measured in fresh normal human plasma and urine, indicating that their formation occurs independent of cyclooxygenase activity. Further studies established that the levels measured in fresh plasma and urine do not arise from ex vivo formation in that the presence of antioxidants in the specimen collecting containers did not suppress the levels measured and levels in urine did not increase during incubation for several days at 37° C. or during storage for up to 6 months at −20° C. In addition, levels were not suppressed by a diet consisted solely of glucose polymers, indicating that the compounds do not arise from dietary sources.

EXAMPLE 2

Reagents

Unlabeled 8-iso-$PGF_{2α}$ was obtained from Cayman Chemical (Ann Arbor, Mich.). Methods to determine the major urinary of 8-iso-$PGF_{2α}$[$^3$H]8-iso-$PGF_{2α}$ (50 Ci/mmol) was commercially prepared from unlabeled 8-iso-$PGF2α$ by SibTek Inc. (Tenafly, N.J.) as a randomly labeled compound. Compound purity and specific activity of the [$^3$H]8-iso-$PGF_{2α}$were confirmed by GC and MS. Amberlite XAD-2 resin and silicic acid (mesh size, 100–200) were obtained from Sigma. All organic reagents were purchased from Baxter (Burdick and Jackson Brand, McGaw Park, Ill.). Pentafluorobenzyl bromide and diisopropyl-ethylamine were obtained from Aldrich. [$^2$H$_9$IN,O-bis(trimethylsilyl)

trifluoroacetamide was purchased from Regis Chemical Co. (Morton Grove, Ill.). 1-Butaneboronic acid was obtained from Applied Science Laboratories (State College, Pa.).

Experimental Strategy for Determining the Metabolic Fate of 8-iso-PGF2α in Humans Because 8-iso-PGF$_{2\alpha}$ exerts potent biological activity, applicants used a strategy whereby only a tracer quantity of 8-iso-PGF$_{2\alpha}$ was infused into a human and 500 μg of unlabeled 8-iso-PGF$_{2\alpha}$ was infused into a monkey. Urine specimens collected from the human and monkey following these infusions were then combined. Using this approach, the relative abundance of the various metabolites reflected by radiolabeled peaks on chromatographic purification would reflect what occurs in humans, whereas the amount of unlabeled material required for structural identification would be derived from the monkey. Although the metabolism of prostanoids in the monkey closely mimics that in humans [Roberts, 1987; Roberts et al. 1977], the approach applicants used eliminated any ambiguity about extrapolating data obtained from determining the metabolic fate of 8-iso-PGF$_{2\alpha}$ in a monkey to that in humans.

Results of Metabolism Study

Infusion of [$^3$H]8-iso-PGF$_{2\alpha}$ into a Human Volunteer

After informed consent was obtained, 20 μCi of [$^3$H]8-iso-PGF$_{2\alpha}$ was infused over one hour in 50 ml of sterile normal saline into an antecubital vein of a normal volunteer. Urine was collected from the beginning of the infusion until six hours after the infusion and stored at −70° C. until processed.

Infusion of 8-iso-PGF$_{2\alpha}$ into a Monkey

600 μg of unlabeled 8-iso-PGF$_{2\alpha}$ combined with 0.6 μCi of [$^3$H]8-iso-PGF$_{2\alpha}$ was resuspended in 200 ml of normal saline sterile and infused into the superficial femoral vein of a 10 kg rhesus monkey over two hours. The small quantity of radiolabeled 8-iso-PGF$_{2\alpha}$ which represented only 3% of the amount of radiolabeled 8-iso-PGF$_{2\alpha}$ infused into humans, was infused along with the unlabeled 8-iso-PGF$_{2\alpha}$ to monitor the time course of excretion of metabolites into the monkey urine. Prior to the procedure, the animal was anesthetized with halothane and remained under anesthesia until infusion was completed. After infusion, urine was collected for six hours in specially designed cage that separates urine from feces. The protocol was approved by the Vanderbilt University Animal Care Committee.

Extraction and Adsorption Chromatography

Initial extraction of urine was performed using Amberlite XAD-2. XAD-2 was suspended in distilled water, and a column (8-cm inside diameter) was packed by sedimentation to a final site of approximately 750 ml. Pooled urine samples (approximately 2000 ml) from both the human and monkey were combined, acidified to pH3 with 1N HCl, and percolated through the column of XAD-2. The column was then washed with 1500 ml of (H$_2$O(pH3), and the radioactivity was eluted with ethanol in 8×100-ml fractions. The ethanol eluates containing significant amounts of radio-activity were then evaporated under reduced pressure. The residue was resuspended in 50 ml of phosphate-buffered saline (pH7.4), acidified with 1N HCl to pH3, and extracted three times with 50 ml of ethyl acetate. The ethyl acetate extracts were combined and applied to a 25-g column (3.2-cm inside diameter) of silicic acid, and radioactivity was eluted with 400 ml of ethyl acetate.

Separation and Purification of 8-iso-PGF$_{2\alpha}$ Metabolites by High Pressure Liquid Chromatography (HPLC)

The ethyl acetate eluate from the silicic acid column was evaporated under reduced pressure, and the residue was then subjected to normal phase HPLC using a 5-μm 30-cm×10-mm Adsorbosphere silica column (Alltech, Deerfield, Ill.) using a gradient solvent system with linear programming of chloroform/acetic acid (100:0.1) to chloroform/methanol/acetic acid (90:10:0.1) over three hours at a flow rate of 4 ml/min. The major radioactive peak eluted was then subjected to reversed phase HPLC using a 5 μm 25-cm×4.6-mm Econosil C-18 column (Alltech) with an isocratic solvent system of water/acetonitrile/acetic acid (80:20:0.1) at a flow rate of 1 ml/min. The single radioactive peak that eluted was then converted to a methyl ester with ethereal diazomethane and rechromatographed on reversed phase HPLC using the same column noted above with a mobile phase of water/acetonitrile (80:20) at a flow rate of 1 ml/min.

Mass Spectrometric Analysis of Major Urinary Metabolite of 8-iso-PGF$_{2\alpha}$ The major urinary metabolite of 8-iso-PGF$_{2\alpha}$ was analyzed by GC-negative ion chemical ionization-MS and by electron ionization-MS. For negative ion chemical ionization analysis, the compound was converted to the pentafluorobenzyl ester trimethylsilyl ether derivative. Catalytic hydrogenation was performed as described previously [Morrow et al. 1990b]. Analysis was performed on a Nermag R10-10 C mass spectrometer interfaced with a DEC-PDP computer. GC was carried out using a 15-m, 0.25-μm film thickness, DB-1701 fused silica capillary column (J & W Scientific, Folsom, Calif.) as described [Morrow et al. 1990b]. Electron ionization-MS of the methyl ester trimethylsilyl ether derivative of the metabolite was carried out as described previously using a Finnigan Incos 50 mass spectrometer [Morrow et al. 1990b].

Results of Metabolism Study

Infusions of 8-iso-PGF$_{2\alpha}$—The infusions of 8-iso-PGF$_{2\alpha}$ into the human volunteer and the monkey were not associated with any significant changes in blood pressure or pulse rate, and no clinically apparent adverse effects were observed of the total radioactivity infused in the human, seventy-five percent was recovered in the urine in 4.5 hours, and ninety-five percent of the radioactivity infused into the monkey was recovered in the urine in four hours. Urine specimens from both the monkey and human were then combined for isolation and purification of metabolites.

Extraction and Adsorption Chromatography of 8-iso-PGF$_{2\alpha}$ Metabolites

Initial compound isolation was achieved by using Amberlite XAD-2 resin chromatography. After loading the sample and washing the column, compounds were eluted with 8×100-ml aliquots of ethanol. Aliquots 5–7 were found to contain ninety-eight percent of the radioactivity. Subsequently, radioactive material eluting in these fractions was evaporated and resuspended in ethyl acetate for adsorption chromatography on silicic acid. It was found, however, that a significant portion of the radioactivity (approximately one-half) was insoluble in ethyl acetate. In contrast, all of the radioactivity was soluble in phosphate-buffered saline (pH7.4) Thus, after resuspension in buffer, the aqueous phase was acidified to pH3 and extracted with ethyl acetate. Fifty-eight percent of the radioactivity extracted into the organic phase, but forty-two percent remained in the aqueous phase, even after exhaustive extractions with ethyl acetate. This suggested that the unextractable metabolites were highly polar, perhaps in the form of a polar conjugate [Taylor and Sun, 1980].

The material that extracted into ethyl acetate was then applied to a column of silicic acid, and ninety-five percent of the applied radioactivity eluted with 400 ml of ethyl acetate.

HPLC Isolation and Purification of 8-iso-PGF$_{2\alpha}$ Metabolites

Figure 5:
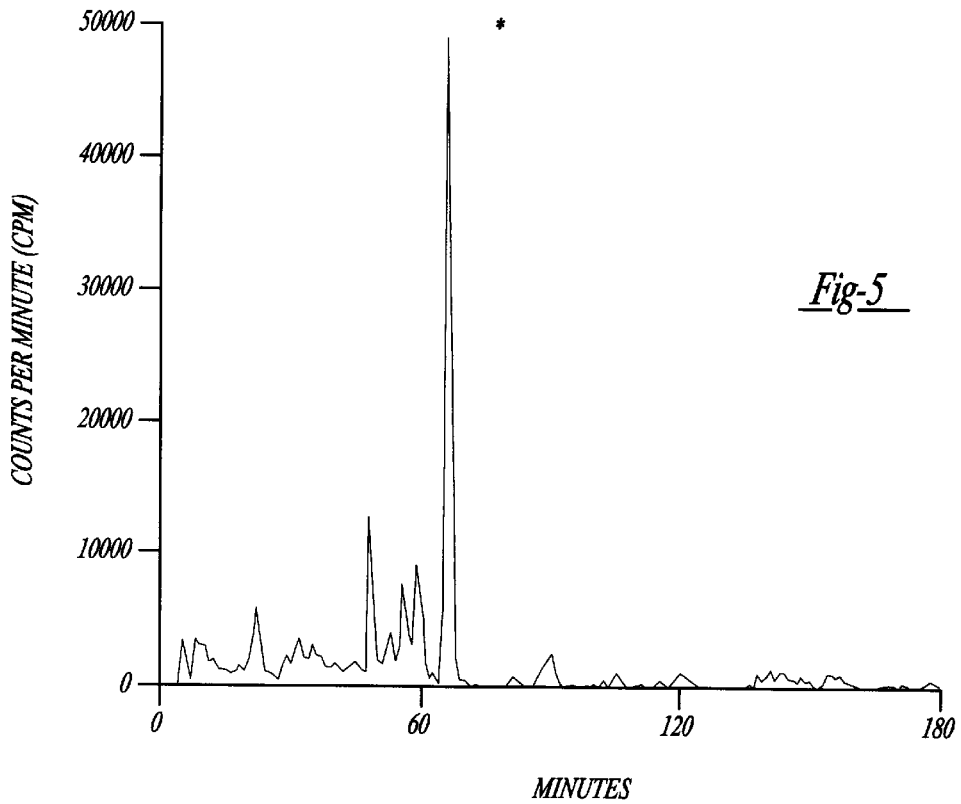
FIG. 5 is a chromatogram illustrating normal phase HPLC analysis of urinary metabolites following extraction of urine and purification by adsorption chromatography.
Figure 6:
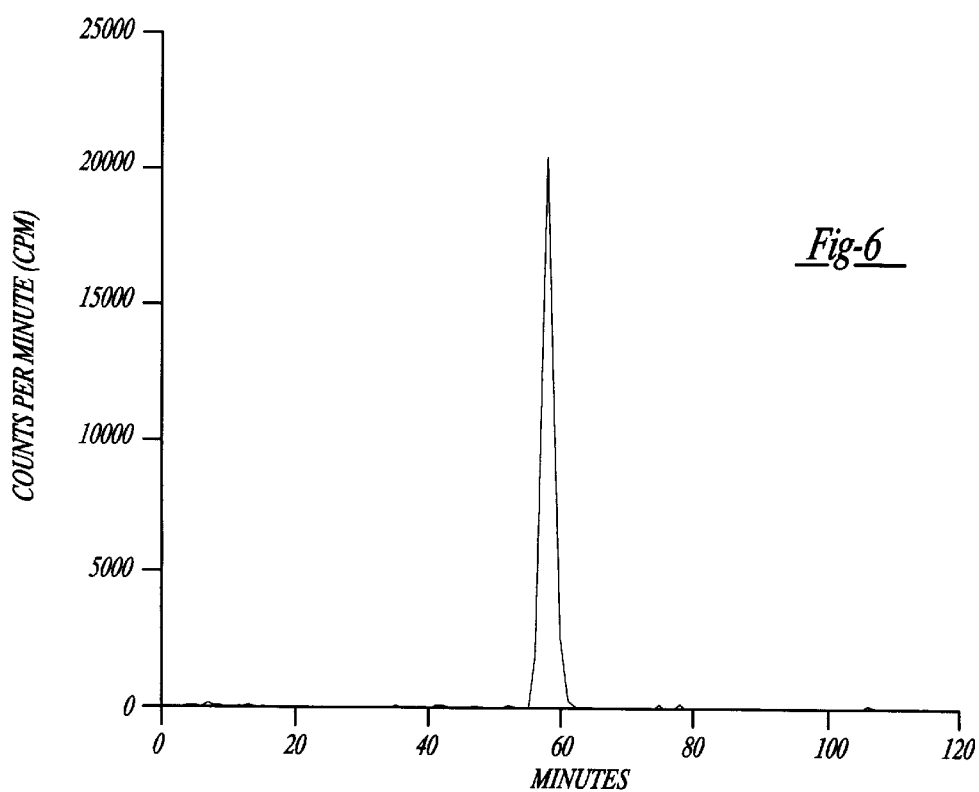
FIG. 6 is a chromatogram illustrating reversed phase HPLC analysis of material that eluted between 65 and 69 minutes in FIG. 5.

Radioactive material eluting from the silicic acid column was initially subjected to normal phase HPLC, as described under "Experimental Procedures." The chromatogram obtained is shown in FIG. 5. As is evident, the vast majority of radioactivity eluted within the first 90 minutes and multiple radioactive peaks are present. However, there was a single major peak (*) that eluted between 65 and 69 minutes. Material in this peak was then subjected to further purification as a free acid on reversed phase HPLC using an isocratic solvent system of water/acetonitrile/acetic acid (80:20:01.). As shown in FIG. 6, essentially all of the recovered radioactivity (>95%) eluted as a single peak between 56 and 60 minutes.

Material in this peak was then converted to a methyl ester and rechromatographed on reversed phase HPLC using a solvent system of water/acetonitrile (80:20). Virtually all the radioactivity (>95%) eluted as a single peak between 27 and 31 minutes. The fact that the single prominent radioactive peak that eluted between 65 and 69 minutes on the initial normal phase HPLC was found to elute as a single sharp peak on the two subsequent reversed phase HPLC purification steps suggested that this was a single compound and represented the major urinary metabolite of 8-iso-PGF$_{2\alpha}$. This compound comprised twenty-nine percent of the total recovered extractable radioactivity present in the urine.

Figure 7A:
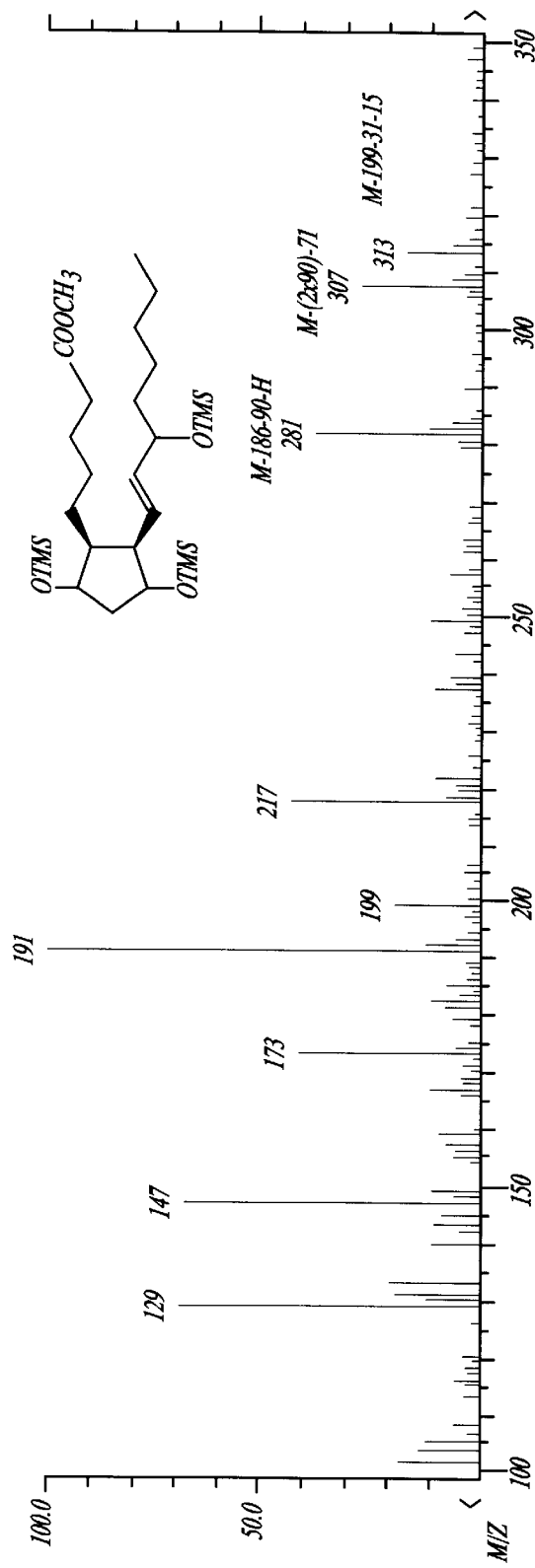
FIG. 7 illustrates the electron ionization mass spectrum of the methyl ester trimethylsilylether derivative of the major urinary metabolite of 8-iso-$PGF_{2\alpha}$.
Figure 7B:
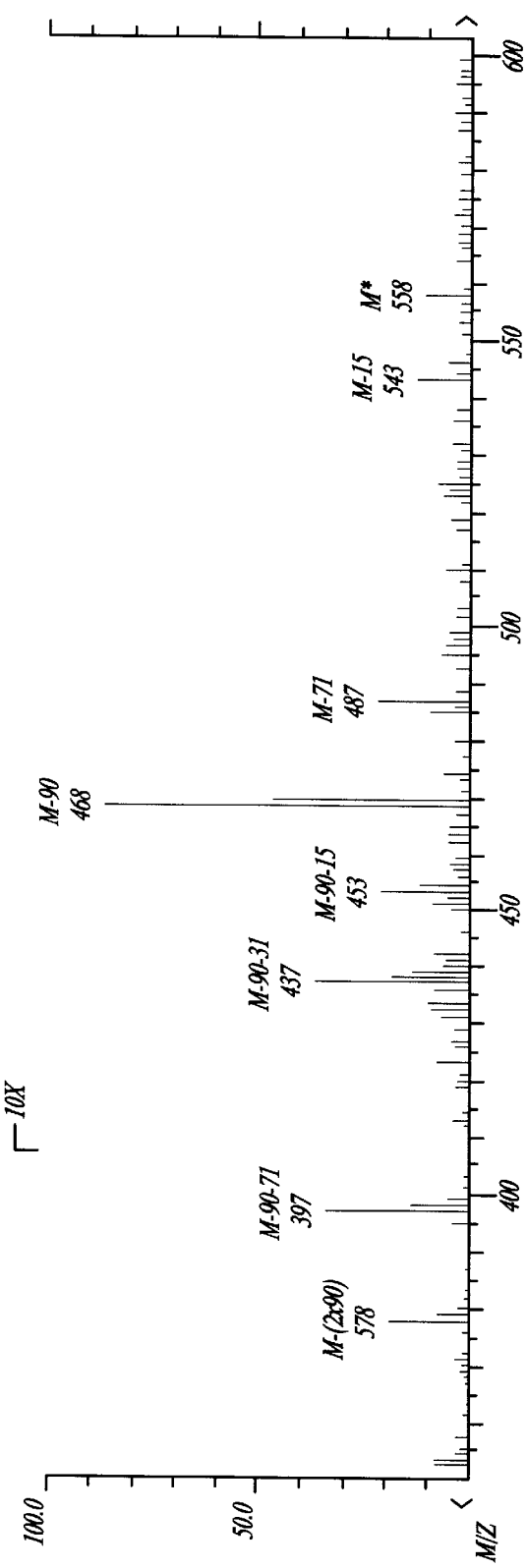

Mass Spectrometric Analysis of the Major Urinary Metabolite of 8-iso-PGF$_{2\alpha}$ This major metabolite was then analyzed by both electron ionization-MS and negative ion chemical ionization-MS. A portion was converted to a methyl ester, trimethylsilyl ether derivative, and analyzed by electron ionization-MS. The mass spectrum obtained for this compound is shown in FIG. 7. A prominent molecular ion was present at m/z 558. Additional prominent ions were also present at m/z 543 (M -15, loss of CH$_3$), m/z 487 (M-71, loss of CH$_2$—(CH$_2$)$_3$—CH$_3$); m/z 468 (M- 90, loss of Me$_3$SiOH); m/z 453 (M-90-15); m/z 437 (M-90 -31, loss of 90+OCH$_3$); m/z 397 (M-90-71); m/z 378 (M-(2×90)); m/z 313 (M-199-31-15, loss of (CH$_2$)$_2$—CHOSiMe$_3$—(CH$_2$)$_4$—CH$_3$+31+15); m/z 307 (M-(2×90)+71): m/z 281 (M-186-90-H, loss of CH$_2$—CH(OSiMe$_3$)—(CH$_2$)$_4$—CH$_3$+90); m/z 217 (Me$_3$SiO—CH=CH—CH=$^+$OSiMe$_3$); m/z 199 ($^+$CH=CH—CH(OSiMe$_3$)—(CH$_2$)$_4$—CH$_3$]; m/z 191 (Me$_3$SiO$^+$=CH—OSiMe$_3$), a rearrangement ion characteristic of F-ring prostanoids [Morrow et al. 1990b]; m/z 173 (Me$_3$SiO$^+$=CH—(CH$_2$)$_4$—CH$_3$]; m/z 147, and m/z 129 (Me$_3$SiO$^+$=CH—CH=CH$_2$. On the basis of this mass spectrum, this metabolite was identified as 2,3-dinor-5,6-dihydro-8-iso-PGF$_{2\alpha}$,

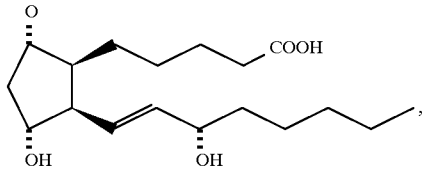

In the mass spectrometric analysis of other eicosanoids, the loss of 186+H from the molecular ion has been noted to occur with fragmentation across the $\Delta^{13}$ double bond [Granstrom et al., 1968; Pace-Asciak, 1989; and Roberts et al., 1981]. The ion at m/z 199 is a typical ion present in the mass spectra of both PGF$_{2\alpha}$ and 8-iso-PGF$_{2\alpha}$ and represents the lower side chain from C13 to C20 [Pace-Asciak, 1989]. The presence of this ion was important in that it indicated that the $\Delta^{13}$ double bond was intact, and thus it was the $\Delta^5$ double bond that has been reduced.

It is of interest that the $\Delta^5$ double bond is reduced in this metabolite, which is major metabolite of 8-iso-PGF$_{2\alpha}$. In previous metabolism studies of other prostanoids and thromboxane B$_2$ in nonhuman primates and humans, only very minor metabolites of thromboxane B$_2$ have been identified in which the $\Delta^5$ double bond had been reduced [Roberts et al. 1981]. One might speculate that inversion of the upper side chain stereochemistry in 8-iso-PGF$_{2\alpha}$ might render it or 2,3-dinor-8-iso-PGF$_{2\alpha}$ a better substrate for the reductase that reduces the $\Delta^5$ double bond [Green, 1971].

Additional approaches were undertaken to further confirm the identity of this metabolite of 8-iso-PGF$_{2\alpha}$ as 2,3-dinor-5,6-dihydro-8-iso-PGF$_{2\alpha}$. First, analysis of the metabolite as a pentafluorobenzyl ester, trimethylsilyl ether derivative by negative ion chemical ionization-MS generated a major fragment ion of 543 Da, representing the expected M-181 ion (loss of CH$_2$C$_6$F$_5$), as would be expected. Second, analysis of the compound as a [$^2$H$_9$] trimethylsilyl ether derivative resulted in a shift of the m/z 543 peak to greater than 27 Da, indicating the presence of three hydroxyl groups. Third, when the compound was analyzed following catalytic hydrogenation, there was disappearance of the m/z 543 peak and the appearance of a new intense peak 2 Da higher at m/z 545, indicating that the compound contained a single double bond. Finally, analysis of the compound after reaction with 1-butaneboronic acid resulted in the disappearance of the m/z 543 ion and the appearance of a major ion at m/z 465, indicating the formation of a cyclic boronate derivative with the cis-cyclopentane ring hydroxyls. Collectively, these results provided additional confirmatory evidence that the metabolite contained the functional groups and the number of double bonds predicted for 2,3-dinor-5,6-dihydro-8-iso-PGF$_{2\alpha}$.

While the present invention has been described by reference to certain illustrative examples, various modifications and variance within the spirit and scope of the invention will be apparent to those skilled in the art.

Throughout this application, various publication are referenced by citation and number. Full citations for the publication are listed below. The disclosure of these publications in their entireties are hereby incorporated by reference into this application in order to more fully describe the state of the art to which this invention pertains.

The invention has been described in an illustrative manner, and it is to be understood the terminology used is intended to be in the nature of the description rather than of limitation.

Obviously, many modifications and variations of the present invention are possible in light of the above teachings. Therefore, it is to be understood that within the scope of the appended claims, reference numerals are numerals are merely for convenience and are not to be in any way limiting, the invention may be practiced otherwise than as specifically described.

REFERENCES CITED

Ames (1983) *Science*, 221:1256–1264.
Awad et al. (1993) *J. Biol. Chem.*, 268:4161–4169.
Banerjee et al. (1992) *Am. J. Physiol*, 263:H660-H663.
Fukunaga et al. (1993) *Am. J. Physiol.*, 264:C1619-C1624.
Granstrom et al. (1968) *J. Biol. Chem.*, 243:4104–4108.
Green (1971) *Biochim. Biophys. Acta.*, 231:419–444.
Gutteridge et al. (1990) *Trends. Biol. Sci.*, 15:129–135.
Harman (1981) *Proc. Natl. Acad. Sci. USA*, 76:7124–7128.
Halliwell et al. (1987) The measurement of free radical reactions in humans: some thoughts for future experimentation. *FEBS Letters*, 213:9–14.

Halliwell and Gutteridge (1990) *Methods Enzymol.,* 186:1–85
Kohler & Milstein, (1975).
Levine et al. (1980) *Prostaylandins,* 20:923–934.
Morrow et al. (1995) *N. Engl. J. Med.,* 332:1198–1203.
Morrow et al. (1994a) *J. Biol. Chem.,* 269:4317–4326.
Morrow et al. (1994b) *Biochim. Biophys. Acta.,* 1210:244–248.
Morrow et al. (1992a) *Proc. Natl. Acad. Sci. USA,* 89:10721–10725.
Morrow et al. (1992b) *J. Clin. Invest.,* 90:2502–2507.
Morrow et al. (1991) *Anal. Biochem.,* 193:142–148.
Morrow et al., (1990a) *Proc. Natl. Acad. Sci. USA,* 87:9383–9387.
Morrow et al. (1990b) *Anal. Biochem.,* 184, 1–10.
Pace-Asciak (1989) *Adv. Prostaglandin Thromboxane Leukotriene Res.,* 18:322–327.
Pryor (1989) On the detection of lipid hydroperoxides in biological samples. *Free Radical Biology & Medicine,* Vol. 7, pp. 177–178.
Rich et al. (1979) *The Peptides,* 1:241–261.
Roberts (1987) in *Handbook of Eicosanoids: Prostaglandins and Related Lipids Chemical and Biochemical Aspects,* Part A (Willis, A. L., ed), pp. 233–244, CRC Press Inc., Boca Raton, Fla.
Roberts et al. (1981) *J. Biol. Chem.,* 256:8384–8393.
Roberts et al. (1977) *J. Biol. Chem.,* 252:7415–7417.
Southorn and Powls (1988) *Mayo. Clin. Proc.,* 63:390–408.
Takahashi et al. (1992) *J. Clin. Invest.,* 90:136–141.
Taylor and Sun (1980) *J. Pharmacol. Exp. Ther.,* 214:24–30.

What is claimed is:

1. A method to assess oxidative stress in vivo comprising:
   (a) subjecting phospholipids in a biological sample to reverse phase solid chromatography extraction using a C-18 cartridge,
   (b) eluting prostanoids retained on the C-18 cartridge with a 80:20:0.1 mixture of water/acetonitrile/acetic acid;
   (c) maintaining the eluate of a phospholipids from a fresh sample of lipid containing biological fluid at −20° C.;
   (d) measuring an amount of noncyclooxygenase derived prostanoids present in the eluate of the phospholipids from the fresh sample of lipid containing biological fluid maintained at −20° C.;
   (e) comparing said measured amount of prostanoids with a control; and
   (f) assessing oxidative stress in vivo based on the comparison in step (b).

2. A method as set forth in claim 1 wherein the sample is urine.

3. A method as set forth in claim 1 wherein the sample is a fresh sample of tissue.

4. A method as set forth in claim 1 further including the step of storing the biological sample prior to said measuring step.

5. The method as set forth in claim 1 wherein measurement is by mass spectroscopy.

6. The method as set forth in claim 1 wherein measurement is by immunoassay.

7. A method to assess oxidative stress in vivo comprising:
   (a) measuring the amount of noncyclooxygenase derived prostanoids in a biological sample before the ex vivo development of prostanoids in the sample;
   (b) comparing the measured amount of the noncyclooxygenase derived prostanoids with a control; and (c) assessing oxidative stress in vivo based on the comparison in step (b wherein said prostanoids are selected from the group consisting of:

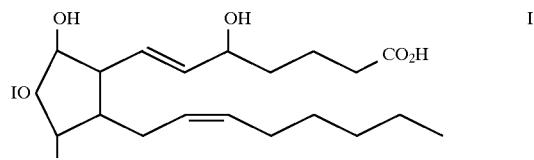

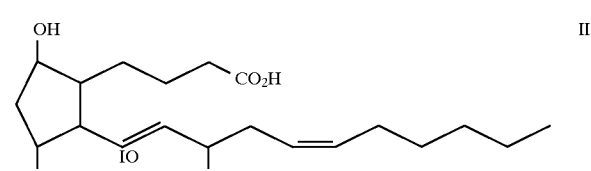

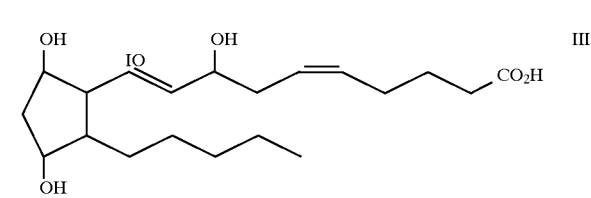

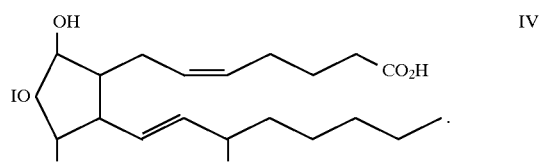

8. A method to assess oxidative stress in vivo comprising:
   (a) measuring the amount of noncyclooxygenase derived prostanoids in a biological sample before the ex vivo development of prostanoids in the sample;
   (b) comparing the measured amount of the noncyclooxygenase derived prostanoids with a control; and
   (c) assessing oxidative stress in vivo based on the comparison in step (b) wherein said prostanoids are selected from the group consisting of:

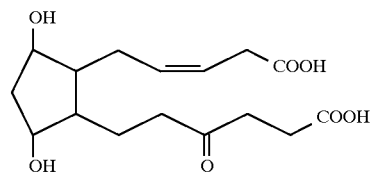

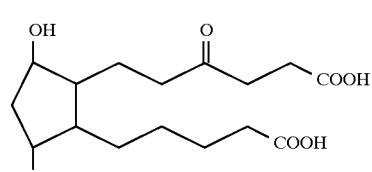

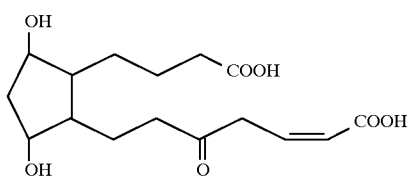

-continued

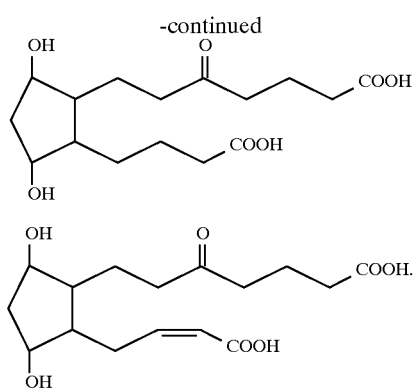

9. A method to assess oxidative stress in vivo comprising:

(a) measuring the amount of noncyclooxygenase derived prostanoids in a biological sample before the ex vivo development of prostanoids in the sample;

(b) comparing the measured amount of the noncyclooxygenase derived prostanoids with a control; and (c) assessing oxidative stress in vivo based on the comparison in step (b) wherein said prostanoid comprises 2,3-dinor-5,6-dihydro-8-iso-prostaglandin $F_{2\alpha}$.

10. A purified and isolated compound of the formula 2,3-dinor-5,6-dihydro-8-iso-prostaglandin $F_{2\alpha}$.

* * * * *